United States Patent [19]

Rogers et al.

[11] 4,198,503

[45] Apr. 15, 1980

[54] 3-CARBAMOYL SUBSTITUTED-7-UREIDO SUBSTITUTED CEPHALOSPORINS

[75] Inventors: Norman H. Rogers, Rudgwick; Robert Stevenson, Dorking, both of England

[73] Assignee: Beecham Group Limited, Great Britain

[21] Appl. No.: 930,217

[22] Filed: Aug. 2, 1978

Related U.S. Application Data

[63] Continuation of Ser. No. 792,129, Apr. 29, 1977, abandoned, which is a continuation of Ser. No. 621,359, Oct. 10, 1975, abandoned.

[30] Foreign Application Priority Data

Nov. 5, 1974 [GB] United Kingdom ............... 49423/74

[51] Int. Cl.² .................. C07D 501/32; C07D 501/34
[52] U.S. Cl. ..................................................... 544/22
[58] Field of Search .......................................... 544/22

[56] References Cited

U.S. PATENT DOCUMENTS

| | | | |
|---|---|---|---|
| 3,227,709 | 1/1966 | Patchett et al. | 544/30 |
| 3,687,949 | 8/1972 | Holdrege | 544/27 |
| 3,741,962 | 6/1973 | Breuer | 544/27 |
| 3,905,963 | 9/1975 | Webber | 544/22 |
| 3,920,640 | 11/1975 | Schorr et al. | 544/22 |
| 3,956,292 | 5/1976 | Cooper et al. | 544/30 |

FOREIGN PATENT DOCUMENTS 2332065 1/1974 Fed. Rep. of Germany.

OTHER PUBLICATIONS

Christensen et al., Chem. Abstracts, vol. 78, p. 420; 159,643m, 5 vol. 79, p. 369, 53,342a.
Imanaka et al., Chem. Abstracts, vol. 80, p. 307; 144,392(d).

*Primary Examiner*—David Wheeler
*Attorney, Agent, or Firm*—Jacobs & Jacobs

[57] ABSTRACT

A class of 3-carbamoyloxymethyl-7-α-acylureido cephalosporins have a broad spectrum of antibacterial activity.

13 Claims, No Drawings

3-CARBAMOYL SUBSTITUTED-7-UREIDO SUBSTITUTED CEPHALOSPORINS

This application is a continuation of application Ser. No. 792,129 filed Apr. 29, 1977, which in turn is a continuation of application Ser. No. 621,359 filed Oct. 10, 1975, and both now abandoned.

This invention relates to cephalosporins which have, in general, a broad spectrum of antibacterial activity, being active against many species of Gram-positive and Gram-negative bacteria. They are, therefore, useful as therapeutic (and, to a lesser extent, prophylactic) agents in animals, including man and poultry. The invention further relates to methods for the preparation of these cephalosporins and to their use in therapy.

Although there are now available a number of semi-synthetic cephalosporins having what is known as broad spectrum activity, no single cephalosporin is yet available which has a clinically useful level of antibacterial activity against all the pathogenic organisms encountered in clinical practice. The search thus continues for broad-spectrum cephalosporins which have advantages, either in improved antibacterial effectiveness or wider spectrum of activity over the available cephalosporins.

In our co-pending British Application Nos. 27970/73 and 48968/73 there is described cephalosporins of formula (I) or a pharmaceutically acceptable salt or ester thereof:

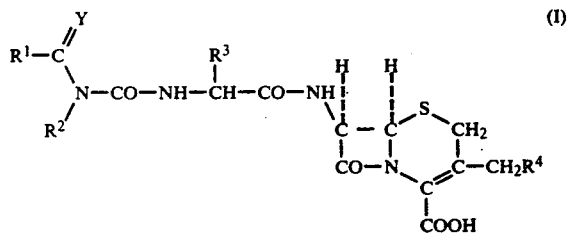

wherein Y is oxygen or sulphur, $R^1$ is an organic radical containing up to 20 carbon atoms; $R^2$ is alkyl having from 1 to 3 carbon atoms, or benzyl; or $R^1$ and $R^2$ together with the carbon and nitrogen atoms to which they are attached form a 5, 6 or 7 membered ring; $R^3$ is phenyl, phenyl substituted by one or more functional groups selected from hydroxy, halogen, nitro, alkoxy containing from 1 to 3 carbon atoms, and amino groups, 2- or 3-thienyl, cycloalkyl having from 3 to 7 carbon atoms or alkyl having from 1 to 4 carbon atoms; $R^4$ is acetoxy or is a carbon, nitrogen or sulphur nucleophile.

The present invention provides cephalosporins of formula (II), or a pharmaceutically acceptable salt or ester thereof:

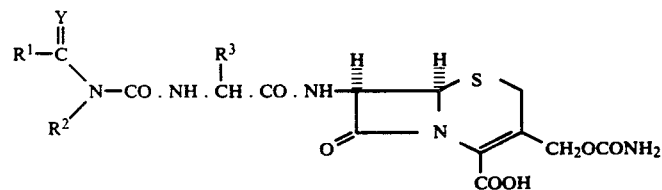

wherein $R^1$, $R^2$, $R^3$ and Y are as defined with reference to formula (I). Preferably Y is oxygen.

In formula (II) the group $R^1$ may for example be $C_{1-10}$ alkyl; $C_{1-10}$ alkenyl; aralkyl or aralkenyl in which the alkyl and alkenyl radicals are $C_{1-10}$ and the aryl radicals are phenyl, thienyl, furyl, pyridyl or substituted phenyl wherein the substituents are selected from $C_{1-3}$ alkyl, $C_{1-3}$ alkoxy, halogen, nitro and amino groups; $C_{1-10}$ alkoxy, $C_{5-7}$ cycloalkoxy; $C_{1-10}$ alkylamino, phenyl; furyl; thienyl; pyridyl; substituted phenyl wherein the substituents are selected from $C_{1-3}$ alkyl, $C_{1-3}$ alkoxy, halogen, nitro and amino groups; functionally substituted $C_{1-10}$ alkyl wherein the functional substituent is, for example, $C_{1-3}$ alkylthio, $C_{1-3}$ alkoxy or phenoxy.

Specifically, the group $R^1$ may be, for example, methyl, ethyl, n- or iso-propyl, n-, sec- or tert-butyl, n-pentyl, n-hexyl, n-heptyl, ω-methylheptyl, n-octyl, ω,ω-dimethyloctyl, prop-2-enyl, 3-methylprop-2-enyl, 1-methyl-prop-2-enyl, but-2-enyl, oct-2-enyl, 2-phenylethyl, 2-phenylethenyl, 2-($2^1$-methoxyphenyl)ethenyl, 2-($4^1$-nitrophenyl)ethen-yl, 2-($3^1,4^1,5^1$-trimethoxyphenyl)ethenyl, 2-(fur-$2^1$-yl)enyl, 3-phenylpropyl, 1-methyl-2-phenylethenyl, 4-phenylbut-2-enyl, 5-phenylpent-2-enyl, 1-methyl-5-phenylpent-2-enyl, methoxy, ethoxy, n- or sec- or tert-butoxy, n-pentoxy, n-hexyloxy, cyclohexyloxy, methylamino, dimethylamino, phenyl, 2-methoxyphenyl, 2-chlorophenyl, 2-methoxyphenyl, 3,4,5-tri-methoxy-phenyl, 4-nitrophenyl, 2-methylphenyl, 4-methylphenyl, methoxymethyl, ethoxymethyl methylthiomethyl, phenoxymethyl.

The group $R^2$ in formula (II) may be, for example, methyl, ethyl, allyl or benzyl. Preferably $R^2$ is methyl.

When $R^2$ and $R^1$ are taken together with the carbon and nitrogen atoms to which they are joined, the ring which is formed may be, for example, one of the following:

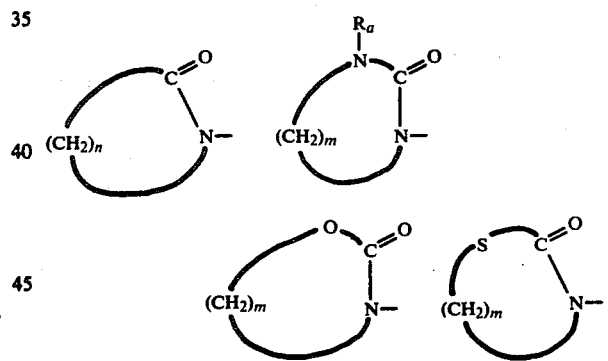

in which n is an integer from 3 to 5 and m is an integer from 2 to 4 and $R_a$ is hydrogen, $C_{1-3}$ acyl or $C_{1-3}$ alkylsulphonyl. Preferably the ring formed is imidazolidin-2-on-yl, 3-acetylimidazolidin-2-on-1-yl, 3-methylsulphonylimidazolidin-2-on-1-yl or hexahydroazepin-2-on-1-yl.

The group $R^3$ in formula (II) may be, for example, phenyl, 4-hydroxyphenyl, 3-chloro-4-hydroxyphenyl, 4-nitrophenyl, 4-aminophenyl, 2-thienyl, 3-thienyl, cyclopropyl, cyclohexyl, cyclohexa-1,4-dienyl, iso-propyl or methyl group. Preferably $R^3$ is phenyl, 4-hydroxyphenyl, 3-chloro-4-hydroxyphenyl or 3-thienyl.

Preferably the configuration of the carbon atom to which the group $R^3$ is attached is D.

Suitable pharmaceutically acceptable salts include the sodium, potassium, calcium, magnesium or aluminium salts and ammonium or substituted ammonium salts, e.g. those with trialkylamines such as triethylamine, procaine, dibenzylamine and triethanolamine.

In case of compounds (II) which contain a basic nitrogen site in the side chain, acid addition salts may also be formed. Such salts include, for example, inorganic salts such as the sulphate, nitrate, phosphate, borate and hydrohalides, e.g. hydrochloride, hydrobromide and hydroiodide and organic salts such as the acetate, oxalate, tartrate, malate, citrate, succinate, benzoate, ascorbate and methanesulphonate.

Suitable pharmaceutically acceptable esters include especially those which break down readily in the human body to leave the parent acid, e.g. acyloxyalkyl esters such as acetoxymethyl, pivaloyloxymethyl, α-acetoxyethyl, α-acetoxybenzyl and α-pivaloyloxymethyl and alkoxycarbonylalkyl esters such as methoxycarbonyloxymethyl or α-methoxycarbonyloxyethyl esters. Other suitable esters of the readily hydrolysable type include lactone, thiolactone and dithiolactone esters (i.e. compounds of formula (II) wherein the 4-carboxy group is esterified as:-

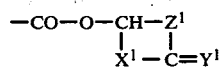

wherein $X^1$ and $Y^1$ are oxygen or sulphur and $Z^1$ is a divalent radical especially the phthalide and substituted phthalide esters e.g. 5,6-dimethoxy-phthalide esters.

The compounds of formula (II), it will be noted, fall into two structural classes, namely those wherein the group $R^1$ is joined to the carbonyl group via a C—C bond and those wherein it is joined via an N—C bond.

The compounds of this invention may be prepared by reacting a compound of formula (III) or a salt, ester or silyl derivative thereof:

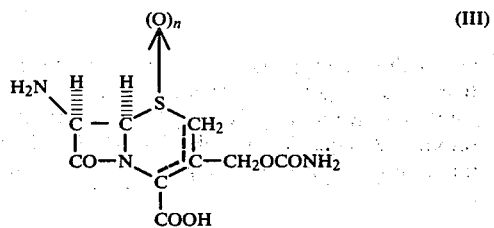

wherein the dotted line represents a bond in the 2- or 3-position and n is 0 or 1 with a reactive N-acylating derivative of an acid of formula (IV):

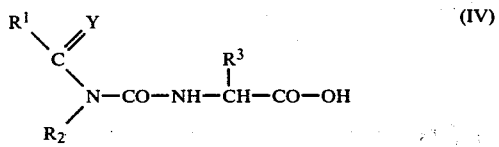

wherein Y, $R^1$, $R^2$ and $R^3$ are as defined in formula (I) and wherein any reactive groups, such as amino and hydroxy groups may be blocked, and thereafter, if necessary carrying out one or more of the following steps:

(i) converting a $\Delta^2$ isomer into the desired $\Delta^3$ isomer;

(ii) removal of any silyl groups by alcoholysis or hydrolysis;

(iii) reduction of a sulphoxide compound to form the desired sulphide compound;

(iv) removal of any blocking groups in the acyl side chain; and (v) conversion of an ester compound to a free acid compound or salt thereof.

By the term "silyl derivative" of compound (II) we mean the product of the reaction between compound (III) and a silylating agent such as a halodialkylsilane, a halotrialkylsilane, a halodialkoxysilane or a halotrialkoxysilane, or a corresponding aryl or aralkylsilane and compounds such as hexamethyldisilazane or bis(trimethylsilyl)acetamide. The silyl derivatives of compound (III) are extremely sensitive to moisture and hydroxylic compounds, and, after reaction with the N-acylating derivatives of the acid (III), the silyl groups of the intermediate acylated compound can be removed by alcoholysis or hydrolysis.

A reactive N-acylating derivative of the acid (IV) is employed in the above process. The choice of reactive derivative will of course be influenced by the chemical nature of the substituents in the acid. Thus, when the acid contains only acid stable groups, an acid halide is a suitable N-acylating derivative preferably the acid chloride.

Such reagents, would however, be avoided when an acid labile group was present in the acid (IV). In such cases a suitable N-acylating derivative is a mixed anhydride. For this purpose particularly convenient mixed anhydrides are the alkoxyformic anhydrides.

Alternative N-acylating derivatives of acid (IV), are activated esters, Such activated esters, for example the ester formed with 1-hydroxybenztriazole or N-hydroxysuccinimide, may be prepared in situ by the reaction of the acid with the appropriate hydroxy compound in the presence of a carbodiimide, preferably dicyclohexylcarbodiimide.

Other reactive N-acylating derivatives of the acid (IV) include the reactive intermediate formed by reaction in situ with a carbodiimide or carbonyldiimidazole, but the literature on the preparation of semi-sythetic penicillins contains examples of other reactive N-acylating derivatives of acids suitable for coupling to 6-APA, for example the acid azide.

It will be understood, of course, that where a free acid of type (II) or salt thereof is desired, it may be convenient to carry out the acylation reaction using an ester of (III) and then to remove the ester group. Vice versa, if an ester is required, it may be convenient to carry out the acylation reaction using compound (III) itself or a salt thereof and thereafter to esterify the free acid.

In the above process, if it is necessary to block any reactive substituents in the acid (IV), conventional chemical blocking groups are known. Thus, if desired, any free amino groups may be blocked by conversion to t-butyloxycarbonyl or benzyloxycarbonylamino groups, or the amino group may be blocked as the nitro group which is later converted to the amino group.

When the compound resulting after N-acylation contains a sulphoxide group at the 1-position of the cephem ring this may be reduced by conventional methods, for example, those described in British Pat. No. 1,280,693. One such method is treatment with triphenylphosphine and acetyl chloride. When the resultant compound is a $\Delta^2$ cephem, the desired $\Delta^3$ cephem may be obtained by treatment of the former with a base, e.g. an alkali metal hydroxide or tertiary amine bases such as pyridine and triethylamine, or by oxidation to the $\Delta^2$ cephem sulphoxide followed by reduction to the $\Delta^3$ cephem. Methods for converting an ester compound to a free acid or base will depend on the particular ester in question, for example acid- or base-hydrolysis as well as enzymically catalysed hydrolysis may be used. However, to minimise isomerisation and side reactions aqueous solvents are better avoided and Lewis acids are preferable as means for de-esterification in appropriate cases.

The intermediates of formula (III) are disclosed inter alia in British Patent Specification No. 1,350,772 and may be prepared by the action of chlorosulphonyl isocyanate with corresponding amine-protected 3-hydroxymethyl cephem. Alternatively, the compounds (III) may be prepared, as described in Belgian Pat. No. 794389, by reacting the amine-protected 3-hydroxymethyl cephem with a substituted isocyanate.

Another method for the preparation of compound (II) is to react a compound of formula (V) or a salt, ester of silyl derivative thereof:

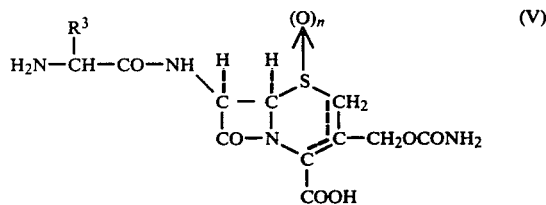

wherein the dotted line represents a bond in the 2- or 3-position $R^3$ and $R^4$ are as defined with respect to formula (I), with a compound of formula (VI):

wherein Y, $R^1$, $R^2$ and $R^3$ are as defined with respect to formula (I), and, thereafter, if necessary, carrying out one or more of the following steps:

(i) converting a $\Delta^2$ isomer into the desired $\Delta^3$ isomer;
(ii) removal of any silyl groups by alcoholysis or hydrolysis;
(iii) reduction of sulphoxide compound to form the desired sulphide compound;

(iv) removal of any blocking groups in the acyl side chain; and (v) conversion of an ester compound to a free acid compound or salt thereof.

The compounds of this invention may also be prepared from the corresponding 3-hydroxymethyl compound by carbamoylation of the hydroxy group. In such a process, a compound of formula (VII) or a salt, ester or silyl derivative thereof:

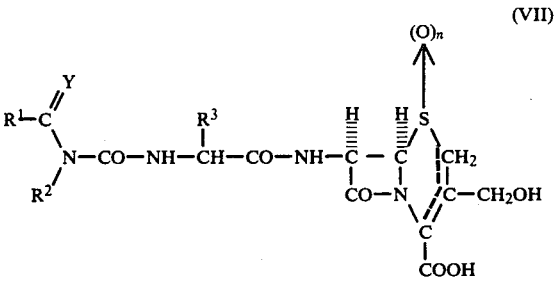

wherein the dotted line represents a bond in the 2- or 3-position, n is 0 or 1, Y, $R^1$, $R^2$ and $R^3$ are as defined in formula (I), and wherein any reactive groups may be blocked, is reacted with an isocyanate of formula $R^5NCO$ where $R^5$ is a group which is removable from the reaction product with compound VII under mild conditions to give compound II and thereafter, if necessary, one or more of the following steps is carried out:

(i) converting a $\Delta^2$ isomer into the desired $\Delta^3$ isomer;
(ii) removal of any silyl groups by alcoholysis or hydrolysis;
(iii) reduction of a sulphoxide compound to form the desired sulphide compound;
(iv) removal of any blocking groups in the acyl side chain; and
(v) conversion of an ester compound to a free acid compound or salt thereof.

Examples of compounds of formula $R^5NCO$ are disclosed in Belgian Pat. No. 794389. Suitable examples include trimethylsilyl isocyanate, $\beta,\beta,\beta$-trichloroethylisocyanate, and chlorosulphonyl isocyanate. The latter is preferred.

The intermediates of formula (VII) may be prepared by the action of an esterase, for example citrus acetyl esterase, on the corresponding 3-acetoxymethyl cephem of formula (VIII):

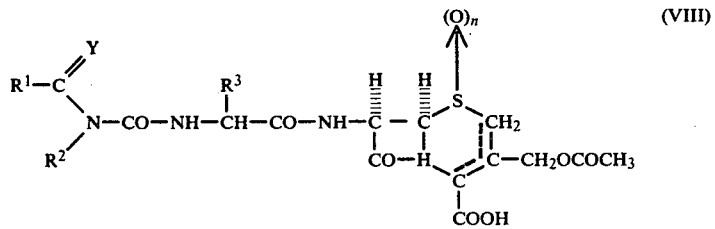

The preparation of compounds (VIII) is described in our British Pat. Nos. 27970/73 and 48968/73.

The compounds of this invention are broad spectrum cephalosporins, i.e. cephalosporins which not only have activity against Gram-positive bacteria but also against a number of clinically important Gram-negative organisms. The preferred compounds of this invention are active against such important organisms as Pseudomonas spp. against which the commercially available cephalosporins are normally inactive. In addition the preferred compounds are active against a number of Gram-negative cephalosporinase producing organisms, e.g. Enterobacter spp., Serratia spp., indole-positive Proteus.

The following Examples illustrate the preparation of some of the compounds of this invention.

EXAMPLE 1

7-Amino-3-carbamoyloxymethyl-3-cephem-4-carboxylic acid (a) 7-(p-Nitrobenzyloxycarbonylamino)cephalosporanic acid N,O-Bis-(trimethylsilyl)acetamide (24.48 ml; 100 m.mole) was added to a suspension of 7-aminocephalosporanic acid (24.48 g.; 90 m. mole) in dry methylene chloride (200 ml) and dry pyridine (18 ml; 225 m. mole). A clear solution was obtained after stirring for 1½ hours at 20° C. This solution was cooled to 5° C. and a solution of p-nitrobenzyl chloroformate (19.5 g.; 90 m. mole) in dry methylene chloride (100 ml) was added dripwise with stirring. The reaction was stirred at 20° C. for 18 hours. Water (20 ml) was added, followed by stirring for ½ hour. The organic layer was separated and evaporated to dryness. The residue was disolved in ethyl acetate and extracted with sodium bicarbonate solution. The aqueous extract was washed with ether, layered with ethyl acetate and with stirring the pH was adjusted to 1.0 with concentrated hydrochloric acid. The ethyl acetate layer was separated, washed with brine, dried over magnesium sulphate, filtered and the filtrate was evaporated to dryness to give a foam. Crystallization from chloroform afforded pure 7-(p-nitrobenzyloxycarbonylamino) cephalosporanic acid (30.2 g.; 74.4% of theory); m.p. 89°–91° C. decomp. δ (DMSO) 8.70 (1H, d, —CONH—), AA'BB' 8.32 and

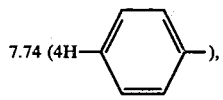

5.65 (2H, m, H$_7$ and α-protons), 5.35 (2H, S, benzylic CH$_2$), 5.20 (1H, d, H$_6$) AB quartet 5.1 and 5.2 (2H, 3-CH$_2$), 3.65 (3H, s, S-CH$_2$—) and 2.14 (3H, S, COCH$_3$); γmax (nujol) 1780 (β-lactam C═O), 1700, 1520 (NO$_2$)cm$^{-1}$; λ max (EtOH) 266 nm (εm 15,194). Biochromatography in butanol, ethanol, water (4:1:5) revealed a single zone at R$_f$=0.43 against *Bacillus Subtilis.*

(b) 3-Hydroxymethyl-7-(p-nitrobenzyloxycarbonylamino)-3-cephem-4-carboxylic acid 7-(p-Nitrobenzyloxycarbonylamino)cephalosporanic acid (1.0 g.; 2.2 m. mole) was dissolved in water (25 ml) by the addition of 1 N sodium hydroxide solution to give a final pH of 7.0. Citrus acetyl esterase enzyme solution (50 ml) was added and the solution was stirred at 26° C. for 18 hours with the pH maintained at 7.0 by automatic addition of N/5 sodium hydroxide solution. Sodium chloride (10 g.) was dissolved in the reaction mixture, which was layered with ethyl acetate and with stirring the pH was adjusted to 1.5 with 5 N hydrochloric acid. The ethyl acetate layer was separated, washed with brine, dried over magnesium sulphate. The solution was concentrated in vacuo and cooled in the refrigerator. A crystalline solid was obtained. This was filtered off washed with cold ethyl acetate, ether and dried in vacuo. (0.60 g.; 66.2% of theory). Thin layer chromatography in chloroform, acetone, acetic acid (50:50:7) revealed a single spot at R$_f$=0.1. δ (DMSO) 8.62 (1H, d, CONH), AA'BB' 8.3 and 7.7

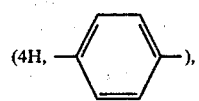

5.52 (2H, m, H$_7$ and α-protons), 5.3 (2H, s, benzylic CH$_2$), 5.1 (d, 1H, H$_6$), 5.43 (2H, s, 3-CH$_2$) and 3.62 (2H, s, S-CH$_2$); β max (nujol) 1770 (β lactam C═O), 1720, 1690, 1520 (NO$_2$)cm$^{-1}$.

(c) 3-Carbamoyloxymethyl-7-(p-nitrobenzyloxycarbonylamino)-cephem-4-carboxylic acid 3-Hydroxymethyl-7-(p-nitrobenzyloxycarbonylamino) 3-cephem-4-carboxylic acid (2.0 g.; 5 m. mole) was suspended in dry acetonitrile (100 ml) and with stirring was cooled to 0°–5° C. under nitrogen. Chlorosulphonylisocyanate (1.1 ml.; 12.5 m. mole) was added dripwise under nitrogen giving a clear solution almost immediately after the addition. The solution was stirred for 1 hour at 0°–5° C. and evaporated to dryness. The resulting gum was dissolved in aqueous sodium bicarbonate such that the final solution was at pH 1.5. This aqueous solution (150 ml) was layered with ethyl acetate (200 ml) and the mixture was stirred at 20° C. for 18 hours. The ethyl acetate layer was separated, washed with brine, dried over magnesium sulphate and evaporated to dryness to give 3-carbamoyloxymethyl-7-(p-nitrobenzyloxycarbonylamino)-3-cephem-4-carboxylic acid as a cream powder (1.73 g.; 77% of theory). Thin layer chromatography in chloroform, acetone, acetic acid (50:50:7) revealed a single spot at R$_f$=0.11. δ (DMSO) 8.64 (1H, d, CONH), AA'BB' 8.3 and

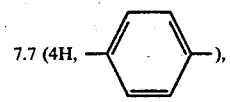

6.54 (2H, S, —CONH$_2$ exchanges D$_2$O), 5.55 (2H, m, H$_7$ and α-protons), 5.28 (2H, s, benzylic CH$_2$), 5.12 (1H, d, H$_6$), AB quartet 4.9 and 4.6 (2H, 3-CH$_2$), and 3.55 (2H, s, S-CH$_2$—), γ max (nujol) 1780 (β-lactam C═O) 1710 (broad), 1520 (NO$_2$)cm$^{-1}$; λ max (EtOH) 266 nm (εm 16220).

(d) 7-Amino-3-carbamoyloxymethyl-3-cephem-4-carboxylic acid

3-Carbamoyloxymethyl-7-p-nitrobenzyloxycarbonylamino-3-cephem-4-carboxylic acid (7.5 g.; 16.5 m. mole) was dissolved in water (100 ml) by adding 1 N sodium hydroxide solution to give a solution with a pH of 7.0. This solution was added to pre-hydrogenated 5% palladium on calcium carbonate catalyst (7.5 g.) in water (100 ml) and hydrogenation was continued for 4½ hours. The reaction mixture was filtered and the filtrate was washed with ether and freeze dried. Thin layer chromatography of the solid residue in chloroform, acetone, acetic acid (50:50:7) revealed one spot with no starting material present. This residue was dissolved in water (25 ml) and the pH of the solution adjusted to 4.0 with 1 N hydrochloric acid resulting in the precipitation of a white solid. The mixture was cooled in the refrigerator and the white solid was collected and dried in vacuo. (1.954 g.). The filtrate was reduced to 5 ml by evaporation and a second crop of solid (0.320 g.) was obtained on cooling. Both crops were dried in vacuo and characterized as 7-amino-3-carbamoyloxymethyl-3-cephem-4-carboxylic acid. δ (TFA) 5.5 (4H, sharp s on top of AB quartet, H$_7$, H$_6$ and 3-CH$_2$-); δ (DMSO) 6.58 (2H, s, OCONH$_2$, exchanges with D$_2$O), 5.00 (2H, m, H$_7$ and α-protons), 4.75 (3H, d overlapping AB quartet, H$_6$ and 3-CH$_2$) and 3.50 (2H, broad s, S-CH$_2$) γ max (KBr) 1790 (β-lactam C=O), 1710, 1605 cn$^{-1}$; λ max (H$_{20}$) 265 nm (εm 7,203).

EXAMPLE 2

7-(D-α-Aminophenylacetamido)-3-carbamoyloxymethyl-3-cephem-4-carboxylic acid Trifluoroacetate Salt A solution of D-α-t-butoxycarboxamidophenylacetic acid (3.443 g.; 13.7 mM) and dry triethylamine (1.91 ml; 13.7 mM) in dry tetrahydrofuran (70 ml) was cooled to −10° C. While stirring under anhydrous conditions isobutyl chloroformate (distilled; 1.80; 13.7 mM) was added. The mixture was stirred at −10° C. for exactly 10 minutes. A cold solution of 7-amino-3-carbamoyloxymethyl-3-cephem-4-carboxylic acid triethylamine salt (prepared by slowly adding triethylamine (1.91 ml; 13.7 mM) to a suspension of 7-amino-3-carbamoyloxymethyl-3-cephem-4-carboxylic acid (3.74 g.; 13.7 mM) in 50% aqueous tetrahydrofuran (70 ml) at 5° C.) was added quickly and the resulting solution was stirred at 5° C. for 1 hour and at 21° C. for an additional 2 hours. The tetrahydrofuran was removed in vacuo and the aqueous solution was then diluted with water and washed with ethyl acetate. The aqueous layer was layered with ethyl acetate, cooled to 5° C. and the stirred mixture was acidified to pH 1.8. The ethyl acetate layer was separated and the aqueous layer was re-extracted with ethyl acetate. The ethyl acetate extracts were combined, washed with brine, dried over magnesium sulphate, filtered and the filtrate was evaporated to dryness in vacuo to give 7-(D-α-t-butoxycarboxamidophenylacetamido)-3-carbamoyloxymethyl-3-cephem-4-carboxylic acid, which was triturated with dry ether and dried in vacuo to give a white solid (3.741 g.; 56%). Thin layer chromatography in chloroform; acetone; acetic acid (50:50:7) showed one component at R$_f$=0.15. δ(DMSO-d$^6$) 9.34 (1H, d, 7-CONH), 7.55 (6H, broad s, Ph and urethane NH), 6.70 (2H, s, CONH$_2$ exchanges in D$_2$O) 5.85 (1H, g, H$_7$), 5.5 (1H, d, α-CH), 5.15 (1H, d, H6) 4.8 (2H, AB quartet, 3-CH$_2$—O—), 3.58 (2H, broad s, —S—CH$_2$—) and 1.47 (9H, s, Bu$^t$); γmax (nujol) 3300 (NH str.) and 1780 (β-lactam C=O)cm$^{-1}$.

7-(D-α-t-Butoxycarboxamidophenylacetamido-3-carba oyloxymethyl-3-cephem-4-carboxylic acid (3.00 g.) was dissolved in trifluoroacetic acid (30 ml) containing anisole (0.05 ml) at 5° C. and the solution was stirred at 5° C. for 6 minutes. The solution was poured into stirred dry ether (300 ml) and the resulting white precipitate was filtered off, washed with ether and dried in vacuo to give 7-(D-α-aminophenylacetamido)-3-carbamoyloxymethyl-3-cephem-4-carboxylic acid trifluoracetate salt (2.12 g., 68.5% of theory). Thin layer chromatography showed one component in butanol; acetic acid; water (12:3:5) R$_f$0.16 and single zones of inhibition against β. Subtilis at R$_f$0.13 and 0.39 in butanol; ethanol; water (4:1:5 top phase) and butanol; acetic acid; water (12:3:5) respectively.

δ(DMSO-d$^6$) 3.55 (2H, m, S-CH$_2$), 4.75 (2H, m, 3-CH$_2$O), 5.0 (2H, m, overlapping α-CH and H$_6$), 5.70 (1H, m, H$_7$), 6.55 (2H, s, CONH$_2$ exchanges with D$_2$O), 7.45 (5H, s, Ph) and 8.1 (4H, broad m, NH$_s$ other than carbamate, exchange with D$_2$O); γmax (KBr) 1770 (β-lactam C=O)cm$^{-1}$; λmax (H$_2$O) 262 (εm 9,000)nm.

EXAMPLE 3

Sodium 3-carbamoyloxymethyl-7-(D-2-(3-cinnamoyl-3-methylureido)-2-phenylacetamido)-3-cephem-4-carboxylate 1N Sodium hydroxide solution (ca 2 ml) was added to a suspension of 7-(D-α-aminophenylacetamido)-3-carbamoyloxymethyl-3-cephem-4-carboxylic acid trifluoroacetate salt (0.52 g., 1 mM) in water (2 ml) and tetrahydrofuran (1 ml) giving a solution at pH 7.0. This clear solution was stirred at 20° C. and was treated dropwise with a solution of N-chlorocarbonyl-N-methylcinnamamide (0.25 g., 1.1 mM) in dry tetrahydrofuran (2 ml) while maintaining the pH at 7.0 with 1N sodium hydroxide solution. When addition was complete the reaction was stirred for a further ½ hour giving precipitation of the product. This was filtered off, was washed with a little ice-cold water and dried in vacuo over phosphorus pentoxide to give sodium 3-carbamoyloxymethyl-7-(D-2-(3-cinnamoyl-3-methylureido)-2-phenylacetamido)-3-cephem-4-carboxylate (0.38 g. 61.7% of theory). Thin layer chromatography showed one main component in butanol; acetic acid; water (12:3:5) R$_f$0.48 and a single zone of inhibition against B. subtilis at R$_f$0.35 in butanol; ethanol; water (4:1:5 top phase). δ(DMSO-d$^6$) 10.30 and 9.55 (2H, d's, —CONH—), 7.55 (12H broad m, aromatic and olefinic protons), 6.70 (2H, broad s, —CONH$_2$ exchanges in D$_2$O), 5.80 (2H, m, C$_7$ and α-protons), 4.95 (3H, m, C$_6$ and —CH$_2$OCO— protons) and 3.47 (5H, singlet covering a multiplet, C$_2$ methylene and >N-CH$_3$); γmax (KBr) 1760 (β-lactam C=O)cm$^{-1}$.

EXAMPLE 4

7-(D-2-(3-Benzoyl-3-methylureido)-2-phenylacetamido)-2-carbamoyloxymethyl-3-cephem-4-carboxylic acid Sodium Salt 1N Sodium hydroxide solution (ca 2 ml) was added to a stirred suspension of 7-(D-α-aminophenylacetamido)-3-carbamoyloxymethyl-3-cephem-4-carboxylic acid trifluoroacetate salt (0.52 g.; 1 mM) in water (2 ml) and tetrahydrofuran (1 ml). This clear solution was stirred at 20° C. and a solution of N-chlorocarbonyl-N-methylbenzamide (0.3 g.; 1.5 mM) in dry tetrahydrofuran (2 ml) was added dropwise. The pH of the reaction mixture was maintained at 7.0 throughout by the addition of 1N sodium hydroxide solution. When the reaction was complete, stirring was continued for ¼ hour. The solution was diluted with water (30 ml) and layered with ethyl acetate (40 ml). The pH was adjusted with stirring to 1.8 and the layers were separated. The aqueous layer was re-extracted with ethyl acetate. The ethyl acetate extracts were combined, washed with brine, dried over magnesium sulphate and evaporated to small bulk (20 ml). 2 N Sodium 2-ethylhexanoate in methylisobutylketone (0.5 ml; 1 mM) was added with stirring to give a white precipitate. The mixture was diluted with dry ether (300 ml) and the precipitate of 7-(D-2-(3-benzoyl-3-methylureido)-2-phenylacetamido)-2-carbamoyloxymethyl-3-cephem-4-carboxylic acid sodium salt was filtered off washed with dry ether and dried in vacuo (0.360 g.; 64% of theory). Thin layer chromatography showed one component in chloroform; acetone; acetic acid (50:50:7) and butanol; acetic acid; water (12:3:5) at $R_f$ 0.10 and 0.40 respectively; and single zones of inhibition were observed against B. Subtilis at $R_f$s 0.32 and 0.85 in butanol; ethanol; water (4:1:5; top phase) and butanol; acetic acid; water (12:3:5) respectively. $\delta$(DMSO-$d^6$) 9.95 (1H, d, —CONH—), 9.50 (1H, d, —CONH—), 7.60 (5H, s, Ph), 7.50 (5H, s, Ph), 6.60 (2H, s, —CONH$_2$ exchanges with D$_2$O), 5.60 (2H, m, H$_7$ and $\alpha$ CH), 5.00 (3H, m, H$_6$ and 3-CH$_2$), 3.40 (2H, broad singlet, CH$_2$—S—) and 3.15 (3H, s, CH$_3$—N—) $\gamma$max (KBr) 1760 ($\beta$-lactam C=O), 1680 (broad, amide C=O)cm$^{-1}$; $\lambda$max (H$_2$O) 260 nm ($\epsilon$m=9,969).

EXAMPLE 5

Sodium 3-carbamoyloxymethyl-7-(D-2-(3-phenylpropionyl)-3-methylureido)-2-phenylacetamido)-3-cephem-4-carboxylate 1 N Sodium hydroxide solution (ca 2 ml) was added to a suspension of 7-(D-$\alpha$-aminophenylacetamido)-3-carbamoyloxymethyl-3-cephem-4-carboxylic acid trifluoroacetate salt (0.52 g., 1 mM) in water (2 ml) and tetrahydrofuran (1 ml) giving a solution at pH 7.0. This clear solution was stirred at 20° C. and was treated dropwise with a solution of N-chlorocarbonyl-N-methyl-3-phenyl-propionamide (0.25 g., 1.1 mM) in dry tetrahydrofuran (2 ml) while maintaining the pH at 7.0 with 1 N sodium hydroxide solution. When addition was complete the reaction was stirred for a further $\frac{1}{2}$ hour. The solution was layered with ethyl acetate (5 ml), acidified to pH 1.5 with N hydrochloric acid and the layers were separated. The organic extract was washed with brine (5 ml) then dried over anhydrous magnesium sulphate, filtered and the filtrate treated with 2 N sodium 2-ethylhexanoate in methylisobutylketone (0.5 ml). This mixture was poured into stirred dry ether (200 ml) and the resulting precipitate was removed by filtration and dried in vacuo to give sodium 3-carbamoyloxymethyl-7-(D-2-(3-(3-phenylpropionyl)-3-methylureido)-2-phenylacetamido)-3-cephem-4-carboxylate (0.53 g.; 85.9%). Thin layer chromatography showed one main component in chloroform; acetone; acetic acid (50:50:7) $R_f$ 0.10 and a single zone of inhibition against Sarcina Lutea at $R_f$ 0.38 in butanol; ethanol; water (4:1:5 top phase). $\delta$(DMSO-$d^6$) 10.26 (1H, d, —CONH—), 9.50 (1H, d, —CONH—), 7.50 (5H, s, aromatic protons), 7.39 (5H, s, aromatic protons), 6.65 (2H, s, —CONH$_2$, exchanges in D$_2$O), 5.69 (2H, m, C$_7$ and $\alpha$-protons), 5.03 (1H, s, C$_6$ proton), 4.90 (2H, AB quartet, 3-CH$_2$—O—), 3.27 (5H, singlet covering a multiplet, C$_2$ methylene and >N—CH$_3$) and 3.00 (4H, s, —CH$_2$CH$_2$Ph); $\nu$max (KBr) 1760 ($\beta$-lactam C=O)cm$^{-1}$; $\lambda$max (water) 263 ($\epsilon$m=7,725)nm.

EXAMPLE 6

3-Carbamoyloxymethyl-7-(D-2-(2-oxo-imidazolidinyl-carbonylamino)-2-phenylacetamido)-3-cephem-4-carboxylic acid 1 N Sodium hydroxide solution (ca 2 ml) was added to a suspension of 7-(D-$\alpha$-aminophenylacetamido)-3-carbamoyloxymethyl-3-cephem-4-carboxylic acid trifluoroacetate salt (0.52 g., 1 mM) in water (2 ml) and dimethylformamide (1 ml) giving a solution at pH 7.0. This clear solution was stirred at 20° C. and was treated dropwise with a solution of 1-chlorocarbonylimidazolidone (0.17. g, 1.1 mM) in dry dimethylformamide (2 ml) while maintaining the pH at 7.0 with 1 N sodium hydroxide solution. When addition was complete the reaction was stirred for a further $\frac{1}{2}$ hour then acidified with N hydrochloric acid to pH 1.5 giving precipitation of the required product. This was removed by filtration and dried in vacuo over phosphorus pentoxide to give 3-carbamoyloxymethyl-7-(D-2-(2-oxo-imidazolidinyl-carbonylamino)-2-phenylacetamido)-3-cephem-4-carboxylic acid (0.27 g., 52.1% of theory). Thin layer chromatography showed one main component in butanol; acetic acid; water (12:3:5) $R_f$ 0.25 and a single zone of inhibition against B. Subtilis $R_f$ 0.57 in butanol; acetic acid; water (12:3:5). $\delta$(DMSO-$d^6$) 9.51 (1H, d, —CONH—), 9.24 (1H, d, —CONH—), 7.70 (1H, s, —NH—, exchanges in D$_2$O), 7.46 (5H, s, aromatic protons), 6.66 (2H, s, —CONH$_2$, exchanges in D$_2$O), 5.72 (2H, m, C$_7$ and $\alpha$-protons), 5.08 (1H, d, C$_6$ proton), 5.0 (2H, AB quartet, 3-CH$_2$—O—), 3.8 (2H broad s, —S—CH$_2$—) and 3.51 (4H, m, imidazolidone methylenes); $\gamma$max (KBr) 1785 ($\beta$-lactam C=O)cm$^{-1}$. $\lambda$max (water) 263 ($\epsilon$m=7,856)nm.

EXAMPLE 7

Sodium 3-carbamoyloxymethyl-7-(D-2-(3-(2-methyl-2-butenoyl)-3-methylureido)-2-phenylacetamido)-3-cephem-4-carboxylate 1 N Sodium hydroxide solution (ca 2 ml) was added to a suspension of 7-(D-$\alpha$-aminophenylacetamido)-3-carbamoyloxymethyl-3-cephem-4-carboxylic acid trifluoroacetate salt (0.52 g., 1 mM) in water (2 ml) and tetrahydrofuran giving a solution at pH 7.0. This clear solution was stirred at 20° C. and was treated dropwise with a solution of N-chlorocarbonyl-N-methyl-2-butenamide (0.19 g., 1.1 mM) in dry tetrahydrofuran (2 ml) while maintaining the pH at 7.0 with 1 N sodium hydroxide solution. When addition was complete the reaction was stirred for a further $\frac{1}{2}$ hour. The solution was layered with ethyl acetate (5 ml), acidified to pH 1.5 with N hydrochloric acid and the layers were separated. The organic extract was washed with brine (5 ml) then dried over anhydrous magnesium sulphate, filtered and the filtrate was treated with 2 N sodium 2-ethylhexanoate in methylisobutylketone (0.5 ml). This mixture was poured into stirred dry ether (200 ml) and the resulting precipitate was removed by filtration and dried in vacuo to give sodium 3-carbamoyloxymethyl-7-(D-2-(3-(2-methyl-2-butenoyl)-3-methylureido)-2-phenylacetamido)-3-cephem-4-carboxylate (0.24 g., 42.3%). Thin layer chromatography showed one component in chloroform; acetone; acetic acid (50:50:7) $R_f$ 0.13 and a single zone of inhibition against B. Subtilis at $R_f$ 0.32 in butanol; ethanol; water (4:1:5 top phase). $\delta$(DMSO-$d^6$) 9.82 (1H, d, —CONH—), 9.50 (1H, d, —CONH—), 7.53 (5H, s, aromatic protons), 6.67 (2H, s, —CONH$_2$, exchanges in D$_2$O), 5.70 (3H, m, H$_7$, vinylic and $\alpha$-protons), 5.00 (1H, s, H$_6$), 4.92 (2H, AB quartet, 3-CH$_2$—O—), 3.38 (2H, m, S—CH$_2$—), 3.17 (3H, s, >N-CH$_3$),

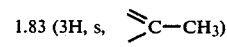

1.83 (3H, s, >C—CH$_3$)

and 1.60 (3H, d, =CH.CH$_3$); $\gamma$max (KBr) 1760 ($\beta$-lactam C=O)cm$^{-1}$. $\gamma$max (water 258) ($\epsilon$m 8.087)nm.

EXAMPLE 8

Sodium 3-carbamoyloxymethyl-7-(D-2-(3-(2-methyl-2-butenoyl)-3-methylureido)-2-phenylacetamido)-3-cephem-4-carboxylate Sodium 3-acetoxymethyl-7-(D-2-(3-(2-methyl-2-butenoyl)-3-methylureido)-2-phenylacetamido)-3-cephem-4-carboxylate (0.5 g., 0.9 mM) dissolved in water (10 ml) and citrus acetylesterase enzyme solution (25 ml) was stirred at 26° C. for 18 hours with the pH maintained at 7.0 by automatic addition of N/5 sodium hydroxide solution. Sodium chloride (3 g.) was dissolved in the reaction mixture, which was layered with ethyl acetate and the pH was adjusted to 1.5 with 5 N hydrochloric acid. The ethyl acetate layer was separated, washed with brine, dried over magnesium sulphate, filtered and the filtrate was evaporated to dryness in vacuo. The product, 3-hydroxymethyl-7-(D-2-(3-(2-methyl-2-butenoyl)-3-methylureido)-2-phenylacetamido)-3-cephem-4-carboxylic acid (0.33 g., 74.7% of theory) was suspended in dry acetonitrile (20 ml) and with stirring was cooled to 5° C. under nitrogen. Chlorosulphonylisocyanate (0.13 ml, 1.5 mM) was added dropwise under nitrogen giving a clear solution almost immediately after the addition. The solution was stirred for 1 hour at 0°–5° C. then evaporated to dryness. The resulting gum was dissolved in water and the pH was adjusted to 1.5 with 5 N sodium hydroxide solution. This aqueous solution (20 ml) was layered with ethyl acetate (20 ml) and the mixture was stirred at 20° C. for 18 hours. The ethyl acetate layer was separated, washed with brine, dried over magnesium sulphate, filtered and the filtrate treated with 2 N sodium 2-ethylhexanoate in methylisobutylketone (0.3 ml). This mixture was poured into stirred dry ether (100 ml) and the resulting precipitate was removed by filtration and dried in vacuo to give sodium 3-carbamoyloxymethyl-7-(D-2-(3-(2-methyl-2-butenoyl)-3-methylureido)-2-phenylacetamido)-3-cephem-4-carboxylate. Thin layer chromatography showed one main component in chloroform; acetone; acetic acid (50:50:7) $R_f$ 0.13 and a main zone of inhibition against B. Subtilis at $R_f$ 0.32 in butanol; ethanol; water (4:1:5 top phase). Further characterisation was consistent with the authentic material.

We claim:

1. A 3-carbamoyloxymethyl-7-α-acylureido cephalosporin of formula (II) or a pharmaceutically acceptable salt or acid addition salt or in vivo hydrolyzable ester thereof:

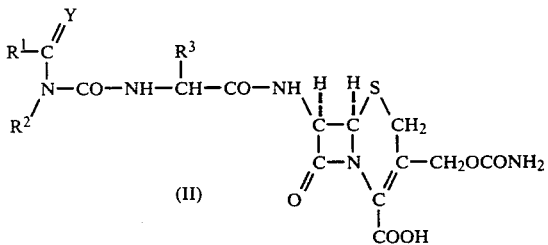

(II)

wherein Y is oxygen or sulphur, $R^1$ is methyl, ethyl, n- or isopropyl, n-, sec, or tert-butyl, n-pentyl, n-hexyl, n-heptyl, ω-methylheptyl, n-octyl, ω,ω-dimethyloctyl, prop-2-enyl, 3-methylprop-2-enyl, 1-methylprop-2-enyl, but-2-enyl-, oct-2-enyl, 2-phenylethyl, 2-phenylethenyl, 2-($2^1$-methoxyphenyl)ethenyl, 2-($4^1$-nitrophenyl)ethenyl, 2-($3^1$, $4^1$, $5^1$-trimethoxyphenyl)ethenyl, 2-(fur-$2^1$-yl)enyl, 3-phenylpropyl, 1-methyl-2-phenylethenyl, 4-phenylbut-2-enyl, 5-phenyl-pent-2-enyl, methoxy, ethoxy, n- or sec-propoxy, n-, sec or tert-butoxy, n-pentoxy, n-hexyloxy, cyclohexyloxy, methylamino, dimethylamino, phenyl, 2-methoxyphenyl, 2-chlorophenyl, 2-methoxyphenyl, 3,4,5-trimethoxyphenyl, 4-nitrophenyl, 2-methoxyphenyl, 4-methylphenyl, methoxymethyl, ethoxymethyl, methylthiomethyl, phenoxymethyl; $R^2$ is alkyl having from 1 to 3 carbon atoms, or benzyl; or $R^1$ and $R^2$ together with the carbon and nitrogen atoms to which they are attached form one of the following ring systems:

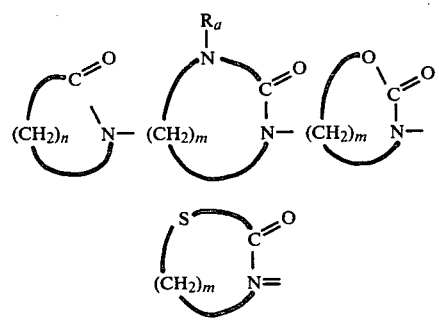

in which n is an integer from 3 to 5 and m is an integer from 2 to 4 and $R_a$ is hydrogen, $C_{1-3}$ alkyl, $C_{1-3}$ acyl or $C_{1-3}$ alkylsulphonyl; $R^3$ is phenyl, 4-hydroxyphenyl, 3-chloro-4-hydroxyphenyl, 4-nitrophenyl, 4-aminophenyl, 2-thienyl, 3-thienyl, cyclopropyl, cyclohexyl, cyclohexa-1,4-dienyl, iso-propyl or methyl.

2. A compound as claimed in claim 1 wherein the ring formed is imidazolidin-2-on-1-yl, 3-acetylimidazolidin-2-on-1-yl, 3-methylsulphonylimidazolidin-2-on-1-yl or hexahydroazepin-2-on-1-yl.

3. A compound as claimed in claim 1 wherein $R^3$ is phenyl, 4-hydroxyphenyl, 3-chloro-4-hyroxyphenyl, 4-nitrophenyl, 4-aminophenyl, 2-thienyl, 3-thienyl, cyclopropyl, cyclohexyl, cyclohexa-1,4-dienyl, iso-propyl or methyl group.

4. A compound as claimed in claim 1 wherein Y is oxygen.

5. A compound as claimed in claim 1 wherein the configuration of the carbon atom to which the group $R^3$ is attached is D.

6. A compound as claimed in claim 1 in the form of a sodium, potassium, magnesium or aluminium salt.

7. A compound as claimed in claim 1 wherein the ester is acetoxymethyl, pivaloyloxymethyl, α-acetoxyethyl, α-acetoxybenzyl, α-pivaloyloxyethyl, methoxycarbonyloxymethyl, α-methoxycarbonyloxyethyl, phthalidyl or 5,6-dimethoxyphthalidyl ester.

8. A compound according to claim 1 which is 3-carbamoyloxymethyl-7-(D-2-(3-cinnamoyl-3-methylureido)-2-phenylacetamido)-3-cephem-4-carboxylic acid.

9. A compound according to claim 1 which is 7-(D-2-(3-Benzoyl-3-methylureido)-2-phenyl-acetamido)-2-carbamoyloxymethyl-3-cephem-4-carboxylic acid.

10. A compound according to claim 1 which is 3-carbamoyloxymethyl-7-(D-2-(3-(3-phenyl-propionyl)-3-methylureido)-2-phenylacetamido)-3-cephem-4-carboxylic acid.

11. A compound according to claim 1 which is 3-carbamoyloxymethyl-7-(D-2(2-oxo-imidazolidinyl-carbonylamino)-2-phenylacetamido)-3-cephem-4-carboxylic acid.

12. A compound according to claim 1 which is 3-carbamoyloxymethyl-7-(D-2-(3-(2-methyl-2-butenoyl)-3-methylureido)-2-phenylacetamido)-3-cephem-4-carboxylic acid.

13. A compound according to claim 1 wherein $R^2$ is methyl.

* * * * *